United States Patent [19]

Matolcsy et al.

[11] 4,086,339
[45] Apr. 25, 1978

[54] METAL COMPLEXES OF ANTIMICROBIC EFFECT

[75] Inventors: György Matolcsy; Barna Bordás, both of Budapest; György Bokor, Miskolc; Zsolt Dombay, Miskolc; Zoltán Pintér, Miskolc; Erzsébet Gregar, née Tóth, Miskolc; Julianna Dudás, née Sz. Kiss, Miskolc; Emiliá Nagy, née Gera, Sajobabony; István Fodor, Miskolc, all of Hungary

[73] Assignee: Eszakmagyarorszagi Vegyimuvek, Sajobabony, Hungary

[21] Appl. No.: 639,100

[22] Filed: Dec. 9, 1975

[30] Foreign Application Priority Data
Dec. 11, 1974 Hungary .................... EA 140

[51] Int. Cl.² .................. A01N 9/22; C07D 215/00
[52] U.S. Cl. ...................... 424/245; 260/283 S; 260/288 CF
[58] Field of Search .............. 260/283 S, 288 CF; 424/245

[56] References Cited
FOREIGN PATENT DOCUMENTS
1,288,358  1/1969  Germany.

OTHER PUBLICATIONS
Chemical Abstracts, vol. 76 (1972), p. 136697j.

*Primary Examiner*—V. D. Turner

[57] ABSTRACT

Metal complexes having the formula

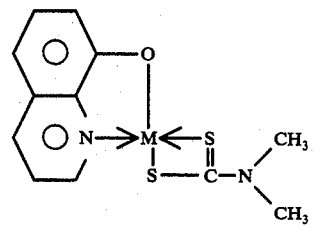

wherein M is a divalent metal atom, and mixtures thereof, have antimicrobial activity and are particularly useful as fungicides.

8 Claims, 1 Drawing Figure

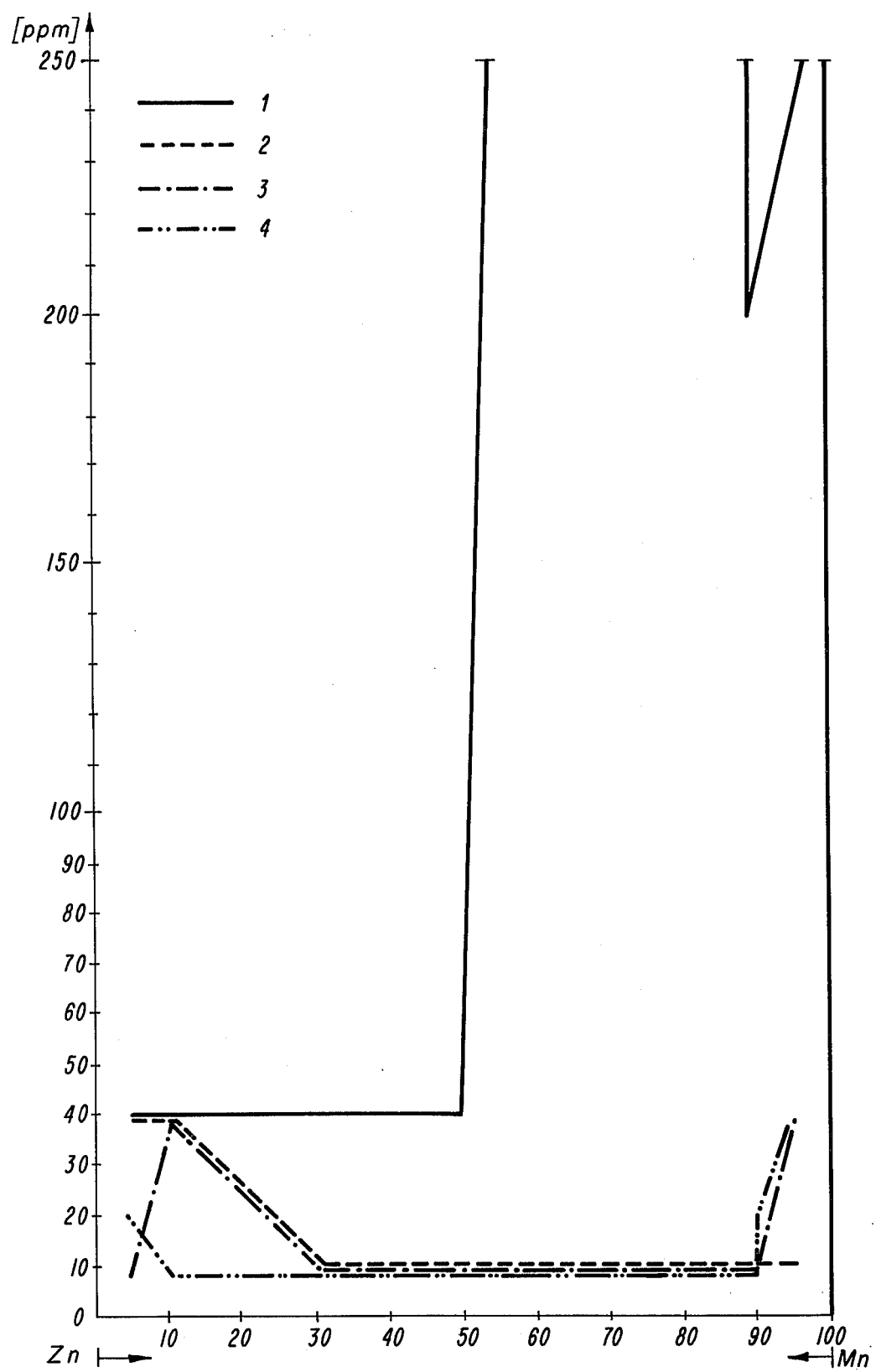

METAL COMPLEXES OF ANTIMICROBIC EFFECT

The invention concerns novel metal complexes of antimicrobic effect, having the general formula I, which are mixed ligand metal complexes of 8-oxyquinoline and diethyl-dithiocarbamic acid. In the formula M is a divalent metal atom, such as Mg, Mn, Fe, Ni, Cu, Zn, Cd, Sn.

The invention also concerns the product of the metal complexes of general formula I.

The formula is:

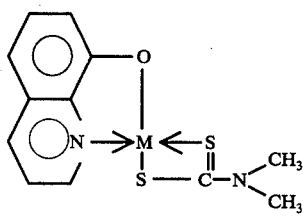

The metal complexes of dialkyl-diethiocarbamic acids and of alkylene-bis-dithiocarbamic acids have become known, and various derivatives of them are widely used as fungicides in plant protection (U.S. Patent Specifications Nos. 1,972.961, 2,317.765, 2,457.674, 2,504.404 and 2,710.822). The most widely used, as leaf fungicides, are the zinc complexes ('Ziram', 'Zineb', 'Propineb'), the manganese complexes ('Maneb') and a product containing a mixture of the two ('Mancoseb'). In spite of widespread use, however, they do not provide adequate protection against many species of fungi, e.g. against Botrytis.

In another connection, 8-oxychinoline and its metal salts have also been known for a long time and several publications describe their fungicidal effect. The possibilities of practical application against fungus diseases of plants have also been studied by many authors. (D. Powell, Plant Disease Reporter, 38, 76–79, /1954/; E. M. Stoddard, Plant Disease Reporter, 41, 536 /1957/; E. M. Stoddard, and R.M. Miller, Plant Disease Reporter, 46, 258–259, /1962/).

8-Oxyquinoline has mostly been investigated in the form of its salts. In one class of these, 8-oxyquinoline plays a cationic role (oxyquinoline sulphate, citrate, salicylate etc.) while in another class the 8-oxychinolinate anion forms a salt with some metal cation, such as copper, cobalt, zinc etc. (C. L. Mason, Phytopathology, 38, 740- 751 /1948/; A. Albert, S. D. Rubboo, R. J. Goldacre, and B. C. Balfour, Brit. J. Phytopathol. 28, 69–87, /1947/; A. Manten, H. L. Klopping, G. J. M. van der Kerk and Antonie van Leeuwenhoek, J. Microbiol. Serol., 17, 58–68 /1951/). Investigations of the structure of the metal salts have proved that they are complexes wherein two 8-oxyquinolinate anions form the ligands of a central metal atom. It has been ascertained that of these metal complexes only copper(II)-oxyquinolinate has a fungicidal effect worth mentioning (D. Powell, Phytopathology, 36, 572–573 /1946/), and for this reason only this compound has become known, under the name 'Oxin'.

In view of the fact that the metal complexes of dialkyldithiocarbamates and of alkylene-bis-dithiocarbamate have not proved to be sufficiently effective against many fungus diseases, there has been widespread research into further possibilities of protection against such fungus diseases. Thus Patent Specification No. 1,288,358 of the Federal Republic of Germany describes a fungicide for protection against Botrytis which consists of a mixture of zinc dimethyl-dithiocarbamate and copper-8-oxyquinolinate.

We have found that the novel mixed ligand metal complexes of 8-oxyquinoline and dimethyl-dithiocarbamate having the general formula I - M in the formula being a divalent metal atom, e.g. Mg, Mn, Fe, Ni, Cu, Zn, Cd, Sn - or mixture of such mixed ligand complexes containing two metal atoms, exhibit a strong microbiotoxic, primarily fungicidal, effect. The novel complexes are characterized by containing two biologically active anions that are different from each other, as mixed ligands.

Further, we have found that the metal complexes of general formula I can be produced by reacting an alkali metal salt of 8-oxyquinoline in a polar organic solvent or in an aqueous solvent with an alkali metal salt of dimethyl-dithiocarbamic acid and a metal halogenide $MHal_2$ — where M has the meaning given above and Hal is a halogen atom, most suitably a chlorine atom — or simultaneously with two such metal halogenides. The reaction is carried out at room temperature, generally at a temperature below 30° C, expediently in an alcoholic or an aqueous-alcoholic medium. As a result of the reaction the desired complex or mixture of complexes separates out from the medium, normally in a crystalline form. The separated product is filtered, washed and dried.

Surprisingly, we have found that the mixed ligand complexes according to the invention are considerably more effective than single-ligand metal complexes of 8-oxyquinoline or dimethyl-dithiocarbamic acid, taken by themselves or in their mixture.

The greater effectiveness manifests itself both in a requirement for a significantly lower concentration of active substances and in suitability the metal complexes according to the invention for inhibiting the germination and proliferation of fungus species against which single-ligand complexes have been practically ineffective (e.g. wheat smut).

In the course of calorimetric tests we have ascertained that the enthalpy change in formation of the mixed-ligand complexes according to the invention is greater than the sum of the enthalpy changes in formation of single-ligand complexes; consequently the complex according to the invention has greater chemical stability than a physical mixture of the two corresponding single-ligand complexes. It is presumed that the increased effectiveness can be functionally related partly to the greater stability and partly to the asymmetric charge distribution of the complex.

The novel, mixed-ligand complex of general formula I may be produced by reacting an alkali metal salt of 8-oxyquinoline in a polar solvent at room temperature with a stoichiometric quantity of an alkali metal salt of dimethyl-dithiocarbamic acid and a halogen salt $MHal_2$ of a divalent metal, the solid product separating out being filtered, washed and dried.

In the course of production one can proceed also by reacting an alkali metal salt of 8-oxychinoline and an alkali metal salt of dimethyl-thiocarbamic acid, not with a stoichiometric quantity of the halogen salt of one metal, but simultaneously in one reaction step with the combined stoichiometric quantity of two metal halogen salts.

The invention further relates to antimicrobic, principally fungicidal, preparations which contain at least one compound having the general formula I as the active substance.

In certain cases, mixtures of compounds of general formula I containing different metal atoms exert a stronger effect, and are therefore preferred in certain areas of application.

The biological effectiveness of the novel, mixed-ligand metal complexes of general formula I were investigated by comparison with the fungicidal effects of commercially available single-ligand zinc dimethyldithiocarbamate ('Ziram') and zinc 8-oxyquinolinate, as well as the equally well-known 1-butylcarbamyl-benzimidazole-2-yl-carbamic acid-methyl ester ('Benomyl').

In the test a modified McCallan method was used (American Phytophathological Society, Committee of Standardization pH Fungicidal Tests, Phytophathology, 33, 419 /1943/). According to this, predetermined quantities of a concentration series prepared from aqueous suspensions of the fungicides to be investigated were applied to plates, the water was evaporated and to the locations of the dried residue a spore suspension of the test fungus was added dropwise. The plates were kept for 24 hours in a humid chamber at constant temperature, then the percentages of the germination and growth were read off microscopically.

The results are given in a percentage concentration ensuring a 50% spore-inhibiting effect ($ED_{50}$), Alternaria tenuis and Botrytis cinerea being used as test fungi, for comparative experiments and the results are shown in Table 1.

Table 1

| No. | Active fungicide | Alternaria tenuis germination | Alternaria tenuis growth | Botrytis cinerea germination | Botrytis cinerea growth |
|---|---|---|---|---|---|
| | | necessary concentration for 50% inhibition | | | |
| 1. | Mixed-ligand Zn 8-oxyquinolate-dimethyl-dithio-carbamate | $10^{-5}$ | $10^{-10}$ | $10^{-10}$ | $10^{-10}$ |
| 2. | Single-ligand Zn 8-oxyquinolate | $10^{-5}$ | $2 \times 10^{-7}$ | $9 \times 10^{-5}$ | $5 \times 10^{-5}$ |
| 3. | Single-ligand Zn dimethyl-dithio-carbamate | $2 \times 10^{-3}$ | $7 \times 10^{-4}$ | $9 \times^{-5}$ | $5 \times 10^{-5}$ |
| 4. | Equimolar mixture of the compounds of 2. and 3. above | $2 \times 10^{-4}$ | $7 \times 10^{-5}$ | $5 \times 10^{-9}$ | $10^{-9}$ |
| 5. | 1-Butylcarbamyl-benzimidazole-2-yl-carbamic acid-methyl ester | $5 \times 10^{-1}$ | $3 \times 10^{-1}$ | $7 \times 10^{-6}$ | $3 \times 10^{-6}$ |

The results in the Table prove that the effect of the mixed-ligand metal complexes according to the invention exceed both the effect of the single-ligand metal complexes (2, 3) and the effect of a physical mixture of the two single-ligand metal complexes. It can also be seen that the fungicidal effect of the commercially very widely used 1-butylcarbamyl-benzimidazole-2-yl-carbamic acid-methyl ester ('Benomyl') is also very considerably exceeded.

We investigated the fungicidal effect of the mixed-ligand metal complexes having the general formula I and containing a central metal atom, and of mixtures of such complexes, for eight fungus species by using the well-known agar diffusion process. The inhibition 'zone' was investigated by means of a dilution series of the complexes, or rather the threshold concentration in ppm where the complex still inhibited the growth of the spores was found (Table 2).

Table 2

| | | Fungus species | | | |
|---|---|---|---|---|---|
| | | A | B | C | D |
| Ex. | Fungicide | threshold concentration in ppm where there is still inhibition (inhibition zone) | | | |
| 1. | Zn-8-oxyquinolinate dimethyl-dithio-carbamate | <2 | <2 | >4 | <2 |
| 2. | Mn-8-oxyquinolinate dimethyl-dithio-carbamate | <2 | >2 | <<2 | <<2 |
| 3. | Cu-8-oxyquinolinate dimethyl-dithio-carbamate | >4 | >80 | >20 | >4 |
| 4. | Cd-8-oxyquinolinate dimethyl-dithio-carbamate | <<40 | >2000 | >200 | >8 |
| 5. | A mixture of: Zn-8-oxychinolinate dimethyl-dithio-carbamate Mn-8-oxychinolinate dimethyl-dithio-carbamate | <<2 | >4 | <<2 | <<2 |
| 6. | A mixture of: Zn-8-oxyquinolinare dimethyl-dithio-carbamate Cu-8-oxyquinolinate dimethyl-dithio-carbamate | >4 | >20 | >4 | <<2 |
| 7. | A mixture of: Mn-8-oxyquinolinate dimethyl-dithio-carbamate Cu-8-oxychinolinate dimethyl-dithio-carbamate | <2 | >4 | '2 | <<2 |
| Standard | 'Zineb' copper -8-oxyquinolate | >2000 40 | >80 1000 | >2000 400 | >80 100 |

A: *Alternaria tenuis*
B: *Aspergillus niger*
C: *Aspergillus tenuis*
D: *Botrytis cinerea*

| | | Fungus species | | | |
|---|---|---|---|---|---|
| | | E | F | G | H |
| Ex. | Fungicide | threshold concentration in ppm, where there is still inhibition (inhibition zone) | | | |
| 1. | Zn-8-oxyquinolinate dimethyl-dithio-carbamate | <2 | >4 | >2 | >4 |
| 2. | Mn-8-oxyquinolinate dimethyl-dithio-carbamate | <2 | >4 | <2 | >2 |
| 3. | Cu-8-oxyquinolinate dimethyl-dithio-carbamate | >20 | >40 | >20 | >20 |
| 4. | Cd-8-oxyquinolinate dimethyl-dithio-carbamate | >80 | >40 | >40 | >8 |
| 5. | A mixture of: Zn-8-oxyguinolinate dimethyl-dithio-carbamate Mn-8-oxyquinolinate dimethyl-di carbamate | >2 | >4 | >2 | >4 |

Table 2-continued

| | | | | | |
|---|---|---|---|---|---|
| 6. | A mixture of:<br>Zn-8-oxyquinolinate<br>dimethyl-dithio-<br>carbamate<br>Cu-8-oxyquinolinate<br>dimethyl-dithio-<br>carbamate | <2 | >20 | '2 | >20 |
| 7. | A mixture of:<br>Mn-8-oxyquinolinate<br>dimethyl-dithio-<br>carbamate<br>Cu-8-oxyquinolinate<br>dimethyl-dithio-<br>carbamate | <<2 | >4 | <20 | <2 |
| Stan-<br>dard | 'Zineb'<br>copper 8-oxyquino-<br>linate | >40<br>100 | >80<br>100 | >40<br>20 | >20<br>100 |

E: *Botrytis allii*
F: *Fusarium culmorum*
G: *Helminthosporium turcicum*
H: *Trichothecium roseum*

The data of the Table unambiguously show the excellent fungicidal effect of the mixed-ligand metal complexes according to the invention, since all seven complexes or mixtures shown inhibit the proliferation of the spores of the eight fungus species at a concentration of less than 200 ppm, — with the exception of one case — and in the overwhelming proportion in a concentration of less than 40 ppm. The complexes according to Examples 1, 2, 5 and 7 inhibit spore proliferation even under 4 ppm, i.e. are effective in exceptionally low concentrations, and their fungicidal effect considerably exceeds that of known fungicides.

Further, we investigated the effect of the novel mixed-ligand metal complexes according to the invention on the very resistant smut fungi (Tilletia spp.), wheat seed being dressed by means of an 80% dust dressing material containing as active substances the mixed-ligand metal complexes or N-methyl-mercury (II)-p-toluenesulphonyl-anilide as a standard ('Granosan').

The wheat seeds used for our experiments were artificially infected with spores of Tilletia caries and Tilletia foetida. The seeds were then dressed in the usual manner with a dose of 200 g/q and the tests were performed by the well-known seed impression method. A nutrient medium applied in a Petri dish in the form of a slurry was dried until its surface became dull and thereafter a seed impression was made by impressing 50–50 dressed seed, with the aid of tweezers. The impressed medium was kept at 12°–18° C and on the 5th, 7th, and 8th day the proportions of impressions with germinating spores were read off.

In parallel with these seed impression experiments, the treated and untreated seeds were planted in cultivation boxes filled with garden soil and the effects of the treatments on the sprouted plants were investigated on the 5th and 10th days after sprouting by measuring the average hight of the plants.

The results of the tests are shown in Table 3.

Table 3

| | Sprouting %  | | Plant height expressed as percentage of height of un-dressed infected control | | Spore germination % of impressions | | |
|---|---|---|---|---|---|---|---|
| Days | 5 | 10 | 5 | 10 | 5 | 7 | 8 |
| Dressed with Zn 8-oxyquinolate dimethyl-dithio-carbamate | 66.5 | 69.0 | 146.7 | 132.0 | Nil | Nil | 0.2 |
| Dressed with N-methyl-HG(II)-p-toluene-sulphonyl-anilide ('Granosan') | 50.5 | 55.5 | 106.2 | 105.8 | Nil | 6.3 | 10.2 |
| Undressed infected seed | 49.0 | 53.0 | 100 | 100 | 79.5 | 94.6 | 97.0 |
| Uninfected control seed | 55.0 | 56.5 | 115.2 | 118 | — | — | — |

According to the results of the measurements the novel mixed-ligand metal complexes provide, on the one hand, a more effective protection against smut than the known dressing agent containing mercury and on the other hand, going beyond that, exert a plant-growth stimulating effect. Thus their use as a dressing agent affords a double advantage.

After ascertaining that the novel mixed-ligand metal complexes exhibit a strong fungicidal effect, we carried out further investigations in the case of three complexes to ascertain on what fungi they exert an effect, in addition to those shown in Tables 1 and 2.

From Table 4 it can be seen that the three investigated mixed-ligand complexes generally exert a well-defined inhibiting effect even at a concentration of 10 ppm in the cases of all seven fungi named.

Table 4

| | 1<br>Zn-8-oxyquino-linate di-methyl-di-thio-car-ba-mate | 2<br>A mixture of Zn and Mn-8-oxy-quinolinate dimethyl-dithio-carbamate | 3<br>Mn-8-oxy-quinolinate dimethyl-dithio-car-ba-mate |
|---|---|---|---|
| Investigated fungi | threshold concentration ppm | | |
| *Cercospora beticola* | 10 | 10 | 10 |
| *Fusarium gramineorum* | $10^2$ | 10 | 10 |
| *Nigrospora oryze* | 10 | 10 | 10 |
| *Septoria lycopersica* | 10 | 10 | 10 |
| *Stemphylium botryceum* | 10 | 10 | 10 |
| *Verticillium sp.* | $2 \times 10^2$ | 10 | 10 |
| *Aspergillus niger* | 10 | 10 | 10 |

Further, mixtures of metallic complexes were investigated wherein the ratios of Zn and Mn were chosen in different ways in order to observe the effect of the ratio to each other of the metals; the measure of the fungicidal activity of mixtures of 8-oxyquinoline-Zn-dimethyl-dithiocarbamate and 8-oxyquinolinate-Mn-dimethyl-dithiocarbamate can be read off in sequence from the graph. The horizontal axis is the percentage composition and the vertical axis is the threshold or limit concentration in ppm. The individual curves show the effect on the following fungi:
1. Fusarium culmorum 2. Trichothecium roseum
3. Helminthosporium turcicum
4. Botrytis ellic With the exception of fusarium culmorum, large inhibition zones were found for the chosen fungi even at very low concentrations, and it may be observed that the effect of complexes of one metal, containing Zn only or Mn only, is smaller than that containing both metals. The ratio of the two metals is expediently between 3:7 – 7:3.

In parallel with the fungicidal effect, an investigation was conducted to show a bactericidal effect. Bacillus subtilis and Pseudomonas tabaci were employed, and the investigation was carried out in a B. subtilis nutrient medium, i.e. 1% meat broth (Oxoid "Lab-Lamco" beef extract) which was solidified with 2% agar-agar. The method of the test was an agar-agar diffusion process.

The result is shown in Table 5, from which it can be seen, that the novel mixed-ligand metal complexes according to the invention have a pronounced bactericidal effect also.

Table 5

| Active substance | Test Bacillus subtilis limit concentration ppm | Test Pseudomones tabaci limit concentration ppm |
|---|---|---|
| Zn-8-oxyquinolinate dimethyl-dithiocarbamate | $10^2$ | $10^4$ |
| Mn 8-oxyquinolinate dimethyl-dithiocarbamate | $10^2$ | $10^2$ |
| A mixture of: Zn-8-oxyquinolinate dimethyl-dithiocarbamate Mn 8-oxyquinolinate dimethyl-dithiocarbamate | $10^2$ | $10^2$ |
| A mixture of: Cd 8-oxyquinolinate dimethyl-dithiocarbamate Mn 8-oxyquinolinate dimethyl-dithiocarbamate | $10^2$ | $10^2$ |

After demonstrating the fungicidal activity of the novel mixed-ligand metal complexes according to the invention we describe the following Examples if processes for their preparation and formulation into fungicides.

The Examples about to be described do not limit the scope of the invention.

EXAMPLE 1

145 g (1 mole) of 8-oxyquinoline were added under stirring to 40 g (1 mole) of sodium hydroxide dissolved in 1500 ml of methanol. The mixture was carried out at room temperature until solution was complete, then a 25% aqueous solution of 143 g (1 mole) of dsodium dimethyl-dithiocarbamate was added to the solution. To the homogeneous solution obtained a solution of 136 g (1 mole) of zinc chloride dissolved in 700 ml methanol was added at a temperature below 30° C, with stirring. After the addition had been completed and the mixture had been left standing for a short time, a thick yellow precipitate separated out which was separated by filtering, washed with water and dried. 331 g of yellow crystalline material was obtained which did not melt or dissociate below 300° C.

Yield: 100% of the theoretical yield of the product, 8-oxyquinolinate-zinc-dimethyl-dithiocarbamate.

The structure of the mixed ligand metallic complexes according to the invention was examined using the product obtained according to Example 1 as a model compound with the following four methods:
  (a) Elemental analysis
  (b) pH measurements
  (c) Calorimety
  (d) Derivatographic measurements In the tabulated compilation the 8-oxyquinoline is designated as oxin while dimethyl-dithiocarbamate is designated as DDC.

(a) Elemental analysis
  Found: N: 8.10%, 8.02%, S: 18.8%, Zn: 20.1%, Calculated: N: 8.46% S: 19.3%, Zn: 19.8%.

(b) pH measurements:
The basis of the determination is the experimental fact that in an acidic medium the pH of the equilibrium system containing Zn(II)-DDC changes with time, hence the $H^+$-ion can expel the metal ion from the complex. Accordingly, a pH measurement method based on the competition between the metal ion and the proton can be used for the equilibrium investigation. By utilizing the measured pH values the stability constant was calculated by a modified SCOGS programme, as was the concentration distribution of the individual molecular parts of the complex. The results are shown in the table below.

Table

| The stability constant of the Zn(DDC)(oxin) mixed complex, the concentration distribution of individual molecular species | | | |
|---|---|---|---|
| pH | $lg_{111}$ | $\Delta lg_{111}$ | $(Zn^{2+})$ % |
| 4.88 | 14.63 | 0.66 | 34.4 |
| 5.02 | 14.53 | 0.56 | 26.2 |
| 5.47 | 14.47 | 0.50 | 21.8 |
| 5.86 | 14.70 | 0.73 | 12.6 |

| $pH_o$ | Zn(oxin) % | Zn(oxin)$_2$ % | (Zn/DDC) % | Zn(DDC)$_2$ | Zn(DDC)(oxin) % |
|---|---|---|---|---|---|
| 4.88 | 2.1 | 0.1 | 25.7 | 24.2 | 23.5 |
| 5.02 | 5.1 | 0.7 | 21.1 | 21.4 | 25.5 |
| 5.47 | 5.7 | 1.0 | 19.5 | 22.0 | 30.0 |
| 5.86 | 5.4 | 1.6 | 12.1 | 14.5 | 53.8 |

In the table $lg_{111}$ represents the stability constant of the mixed complex defined below:

$$Zn^{2+} + oxin + DDC = Zn(oxin)(DDC)$$
$$111 = \frac{[Zn(oxin)(DDC)]}{[Zn^{2+}][oxin^-][DDC]}$$

The mixed-ligand complex formation appropriate to the statistical case can be calculated from the constants of the prime complexes

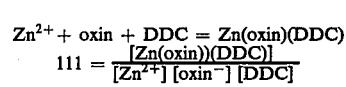

The difference between these constants is the so-called stabilization constant:

$$\Delta lg\beta_{111} = lg\beta_{111} - lg\beta_{111}^+$$

On the basis of the values tabulated in the table:

$$lg\beta_{111} = 14.6 \pm 0.5 \quad \Delta lg\beta_{111} = 0.6 \pm 0.2$$

Thus, the increase in stability in the course of formation of the mixed-ligand Zn(oxin)(DDC) is quite significant. It can be seen further that the process of comples formation becomes complete in the pH range of approximately 4 to 7, and in this way in the system at biological pH always the mixed complex is present. Under such circumstances the relation between the mixed ligand and the prime complexes is expressed by the equilibrium constant $K_M$.

$$Zn(oxin)_2 + Zn(DDC)_2 = 2\ Zn(oxin)(DDC)$$

$$K_M = \frac{[Zn(oxin)(DDC)]^2}{Zn(oxin)_2\ Zn(DDC)_2}$$

The value of $K_M$ on the basis of the above data is $K_M = 60 \pm 30$.

(c) Calorimetry

The investigations were carried out in an alkaline medium at pH = 11, where the dissociation of the complex no longer occurs and the formation of hydroxo-complexes exerts no disturbing effect either. For the investigations an LKB-8700 precision calorimeter was used. In every case the solution contained an equal amount of Zn(II) while the alkaline oxin, and NaDDC, or rather, a mixture thereof were placed in the vial.

As a result of our investigations it can be ascertained that the change in enthalpy of formation of the product according to the invention is greater than the average values obtained in the formation of the prime complexes, which can be ascertained by calculations. The greater change in enthalpy indicates, on the one hand, the favoured character of the formation of the mixed ligand complex, and on the other hand, an increase in the bonding strength.

(d) Derivatographic investigations

Under identical conditions the derivatograms of the product according to the invention and of $Zn(oxin)_2$ and $Zn(DDC)_2$ were prepared. The data are summarized in the tables below:

Table

| Results of the derivatographic tests of the complexes $Zn(oxin)_2$, $Zn(DDC)_2$ and $Zn(DDC)(oxin)$ | | |
|---|---|---|
| | $Zn(oxin)_2$ | |
| °C | Character of dissociation | Weight loss |
| 100 | exothermic | 20.3 |
| 180 | enodthermic | |
| 420 | endothermic | 13.2 |
| | Total: | 33.5 |
| °C | Character of dissociation | Weight loss |
| 100 | endothermic | 2.44 |
| 170 | enodthermic | 2.40 |
| 270 | endothermic | 5.87 |
| 290 | endothermic | 42.07 |
| 455 | exothermic | |
| 520 | exothermic | |
| | Total: | 52.79 |

Table

| Mixed ligand complex of ratio 1:1:1 (2 ligands + 1 metal atom) | | |
|---|---|---|
| °C | Character of dissociaton | Weight loss % |
| 110 | exothermic | 1.30 |
| 180 | endothermic | 6.50 |
| 260 | endothermic | 5.20 |
| 295 | endothermic | 5.20 |
| 295 | endothermic | 6.50 |
| 320 | endothermic | 9.10 |
| 390 | many slight endothermic | 16.9 |
| 520 | Total: | 45.5 |

It can be seen that the derivatogram of the material obtained by a simultaneous precipitation cannot be produced by the super-position of the derivatograms of the two prime complexes, from which it can with justification be inferred that the formation of the mixed complex in the solid phase is complete.

The unambiguous and similar results of the investigations performed with three different methods verify without any doubt that the product described in the invention is a novel compound and not a physical mixture of complexes already known from the literature.

Among the results obtained by the three different investigative methods the calorimetric results are to be highlighted, because in addition to their significance as proving the structure they also show that the product according to the invention is more stable than the physical mixture of the complexes. This extra stability is very significant from a practical view point since it results in a reduction in the rate of dissociation of the product in storage and on application to the plant surface and thus causes an increase in the duration of its effect.

EXAMPLE 2

145 g (1 mole) of 8-oxyquinoline was added with stirring to 40 g (1 mole) of sodium hydroxide dissolved in 1550 ml of methanol and stirred until solution was complete. Thereafter, under stirring, the solution was mixed with a 25% aqueous solution of 143 g (1 mole) of sodium dimethyl-dithiocarbamate and a solution of 198 g (1 mole) of crystalline manganese chloride ($MnCl_2.4H_2O$). dissolved in 750 ml of methanol was added, with cooling, at 20°–25° C. After further mixing the solid complex separated out, and was recovered by filtering, washing and drying.

300 of light brown powdery crystalline material was obtained which did not melt or dissociate up to 300° C.

Yield: 94% of the theoretical yield of the product, is 8-oxyquinolinate-Mn-dimethyl-dithiocarbamate.

Analysis:

Calculation: N 8.77%, S: 20.09%, Mn: 12.7%. Found: N 8.32%, S: 20.12%, Mn: 13.1%.

EXAMPLE 3

145 g (1 mole of 8-oxyquinoline were added under stirring to a solution of 40 g (1 mole) of sodium hydroxide dissolved in 1500 ml of methanol, and stirred until completely dissolved. Thereafter, with stirring the solution was mixed with a 25% aqueous solution of 143 g (1 mole) of sodium dimethyl-dithiocarbamate, and was added under cooling to a solution of 170.5 g (1 mole) of crystalline copper(II) — chloride ($CuCl_2.2H_2O$) in 750 ml methanol. After the addition, the mixture was stirred for another hour. On termination of the stirring a solid powdery crystalline complex separated out. It was recovered by filtering, washed and dried. 310 g of chocolate-brown crystalline material was obtained which did not melt or dissociate up to 300° C.

Yield: 94.5% of theoretical yield the product 8-oxychinolinate-Cu(II)-dimethyl-dithiocarbamate.

Analysis:

Calculated: N: 8.54%, S: 19.56% Cu: 19.38%. Found: N: 8.58%, S: 20.0%, Cu: 19.60%.

EXAMPLE 4

145 g (1 mole) of 8-oxyquinoline was added with stirring to 40 g (1 mole) of sodium hydroxide dissolved in 1500 ml of methanol and stirred until completely dissolved. Thereafter, under stirring the solution was mixed with 143 g (1 mole) of sodium dimethyl-dithiocarbamate as a 25% aqueous solution, and 183.3 g (1 mole) of cadmium chloride dissolved in 750 ml methanol were added, with cooling, at 20°–25° C. After stirring for an hour and leaving the mixture to stand, a crystalline material was separated by filtering, washed with water, and dried. 300 g of light brown powdery crystalline material was obtained which did not dissociate or melt up to 300° C.

Yield: 95.5% of the theoretical yield of the product, 8-oxyquinolinate-Cd-dimethyl-dithiocarbamate.
Analysis:
Calculated: N: 7.44%, S: 17.03%, Cd: 29.92%, Found: N: 7.35%, S: 17.30%, Cd: 30.10%.

EXAMPLE 5

145 g (1 mole) of 8-oxyquinoline were added with stirring to 40 g (1 mole) of sodium hydroxide dissolved in 1500 ml methanol and stirred until completely dissolved. Thereafter the solution was mixed with stirring with 143 g (1 mole) of sodium dimethyl-dithiocarbamate as a 25% aqueous solution, and then under cooling mixed with 178.5 g (0.9 mole) of crystalline manganese chloride ($MnCl_2.4H_2O$) and 13.5 g (0.1 mole) of zinc chloride dissolved in 700 ml of methanol. After stirring for an hour, separated powdery crystalline material was filtered off, washed with water and dried.

295 g of green-brown crystalline material were obtained which did not melt or dissociate up to 300° C.

Yield: 92% of the theoretical yield of the product, a mixture, in a molar ratio of 1:9, of 8-oxyquinolinate-Zn-dimethyl-dithiocarbamate and 8-oxyquinolinate-Mn-dimethyl-dithiocarbamate.
Analysis:
Calculated: N: 8.75%, S: 20.03%, Mn: 15.42%, Zn: 2.09%. Found: N: 8.58%, S: 19.80%, Mn: 15.30%, Zn: 2.11%.

EXAMPLE 6

145 g (1 mole) of 8-oxyquinoline were added under stirring to 40 g (1 mole) of sodium hydroxide in 1500 ml of methanol and stirred until completely dissolved. Thereafter, under stirring, the solution was mixed with 143 g (1 mole) of sodium dimethyl-dithiocarbamate as a 25% aqueous solution, then mixed with cooling with 123 g (0.9 mole) of zinc chloride and 17 g (0.1 mole) of crystalline copper chloride ($CuCl_2.2H_2O$) dissolved in 750 ml of methanol, at 20°–25° C. After stirring for an hour, crystalline material separated out during standing was filtered off, washed with water and dried.

312.5 g of a brown crystalline powdery material were obtained which did not melt or dissociate up to 300° C.

Yield: 95% of the theoretical yield of the product a mixture of 8-oxyquinolinate-Zn-dimethyl-dithiocarbamate and 8-oxyquinolinate-Cu(II)-dimethyl-dithiocarbamate in a molar ratio of 9:1.
Analysis:
Calculated: N: 8.49%, S: 19.43%, Zn: 17.88%, Cu: 1.92%. Found: N: 8.40%, S: 19.60%, Zn: 17.60%, Cu: 2.10%.

EXAMPLE 7

145 g (1 mole) of 8-oxyquinoline were added with stirring to 40 g (1 mole) of sodium hydroxide dissolved in 1500 ml of methanol and stirred until completely dissolved. Thereafter the solution was mixed with stirring with 143 g (1 mole) sodium dimethyl-dithiocarbamate as a 25% aqueous solution, and then under cooling and at a temperature of 20°–25° C added to 178.1 g (0.9 mole) of crystalline manganese chloride ($MnCl_2.4H_2O$) and 17 g (0.1 mole) of crystalline copper chloride ($CuCl_2.2H_2O$) in 750 ml of methanol. Mixing was continued for an hour then the crystalline material separated during standing was filtered off, washed with water and dried. 310 g of brown crystalline powdery material was obtained which did not melt or dissociate up to 300° C.

Yield: 96.5% of the theoretical yield of the product, a mixture of 8-oxyquinolinate-Mn(II)-dimethyl-dithiocarbamate and 8-oxyquinolinate-Cu(II)-dimethyl-dithiocarbamate in a molar ratio of 9:1.
Analysis:
Calculation: N: 8.75%, S: 20.04%, Mn: 15.42%, Cu: 1.99%. Found: N: 8.62%, S: 20.10%, Mn: 15.38%, Cu: 2.05%.

EXAMPLE 8

80 kg of 8-oxyquinolinate-Zn-dimethyl-dithiocarbamate, 20 kg of talc and 1 kg of paraffin oil were mixed in a ball-mill for an hour and ground. 100 kg of product containing 80% of active substance were obtained, utilizable for dust dressing with a dose of 200 g/100 kg of seed.

EXAMPLE 9

50 kg of 8-oxyquinolinate-Mn-dimethyl-dithiocarbamate, 41 kg of 'Tensia N-300', 2 kg 'Aerosil', 3 kg of 'Totanin B', 2 kg of 'Tensiofix LC Spec' and 3 kg of 'Tensopol SP — USP' were added to a ball-mill and ground for 3 hours. 100 kg of wettable powder were obtained containing 50% of active substance, utilisable as a fungicide, sprayed in water, for protection against Botrytis cinerea.

EXAMPLE 10

A mixture of 20 kg of 8-oxyquinolinate-Zn-dimethyl-dithiocarbamate and 8-oxyquinolinate-Mn-dimethyl-dithiocarbamate was charged into a ball-mill together with 2.5 kg of 'Poliglikol' 1000, 10 kg of 'Emulsogen' N and 67.5 kg of 'Vaseline' oil and ground for 2.5 hours. 100 kg of an oily suspension containing 20% of active ingredient were obtained.

EXAMPLE 11

A mixture of 45 kg of 8-oxyquinolinate-Mn-dimethyl-dithiocarbamate and 8-oxyquinolinate-Cu(II)-dimethyl-dithiocarbamate were charged into a ball-mill togehter with 10 kg of 'Emulsogen M', 10 kg of ethylene glycol and 35 kg of water and ground for three hours. 100 kg of an aqueous suspension was obtained which contained 45% active substance and which could be sprayed when diluted with water.

The materials used in Examples 8 to 11:

| a. | carriers: | 'Tensia N-300' |
| | | 'Aerosil' |
| b. | dispersing agents: | 'Totanin B' |
| | | 'Tensofix LX Spec' |
| | | 'Emulsogen M' |
| | | 'Poliglikol' 1000 |
| c. | wetting agents: | 'Tensopol SP-USP' |

We claim:
1. A compound selected from the group consisting of metal complexes of the formula I

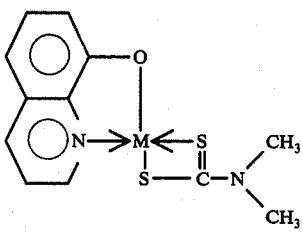

wherein M is a divalent metal atom, and mixtures thereof.

2. The compound, as claimed in claim 1, wherein M is Mg, Mn, Fe, Ni, Cu, Zn, Cd or Sn.

3. A composition for inhibiting growth of a microorganism selected from the group consisting of fungi and bacteria comprising (a) an amount sufficient to inhibit the growth of said organism of a compound selected from the group consisting of metal complexes of the formula I

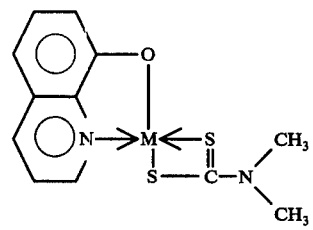

wherein M is a divalent metal atom, and mixtures thereof and (b) a carrier therefor.

4. The composition, as claimed in claim 3, wherein M is Mg, Mn, Fe, Ni, Cu, Zn, Cd or Sn.

5. The composition, as claimed in claim 3, wherein the microorganism is a fungus.

6. A process for inhibiting the growth of a microorganism selected from the group consisting of fungi and bacteria comprising the step of contacting said organism with an amount sufficient to inhibit its growth of a compound selected from the group consisting of metal complexes of the formula I wherein M is a divalent metal atom, and mixtures thereof.

7. The process, as claimed in claim 6, wherein M is Mg, Mn, Fe, Ni, Cu, Zn, Cd or Sn.

8. The process, as claimed in claim 6, wherein the organism is a fungus.

* * * * *